(12) United States Patent
Newsome

(10) Patent No.: US 6,176,581 B1
(45) Date of Patent: Jan. 23, 2001

(54) FLASH RECOVERY TIMER AND WARNING DEVICE

(76) Inventor: David A. Newsome, 1701 Oriole, New Orleans, LA (US) 70122

( * ) Notice: Under 35 U.S.C. 154(b), the term of this patent shall be extended for 0 days.

(21) Appl. No.: 09/409,027

(22) Filed: Sep. 29, 1999

(51) Int. Cl.[7] .................................................. A61B 3/02
(52) U.S. Cl. ............................................................ 351/224
(58) Field of Search .................................... 351/200, 201, 351/202, 203, 211, 221, 237, 224, 246; 600/558

(56) References Cited

U.S. PATENT DOCUMENTS

| | | | |
|---|---|---|---|
| 2,232,316 | 2/1941 | Deederer | 88/20 |
| 2,247,653 | 7/1941 | Feldman | 88/20 |
| 2,283,769 | 5/1942 | Schwanzel | 350/96.1 |
| 3,684,355 | 8/1972 | Molner | 351/36 |
| 4,545,658 | 10/1985 | Weiss | 351/222 |
| 4,764,007 | 8/1988 | Task | 351/243 |
| 5,065,767 | 11/1991 | Maddess | 128/745 |
| 5,080,478 | 1/1992 | O'Brien et al. | 351/224 |
| 5,598,235 | * 1/1997 | Heijl et al. | 351/224 |
| 5,822,037 | * 10/1998 | Barad | 351/224 |
| 5,989,194 | * 11/1999 | Davenport et al. | 600/558 |

* cited by examiner

Primary Examiner—George Manuel
(74) Attorney, Agent, or Firm—Garvey, Smith, Nehrbass & Doody, L.L.C.

(57) ABSTRACT

A flash recovery timer and warning device is a hand-held electronic device using a bright flash to create a temporary glare-type vision blur to the eye to be tested and a target and timer to determine the amount of time required for the eye to recover after the flash. The device has a voice chip that, in addition to the timer display, warns that the vision recovery time is unusually prolonged and professional help should be sought. Other clinical applications may be useful.

21 Claims, 1 Drawing Sheet

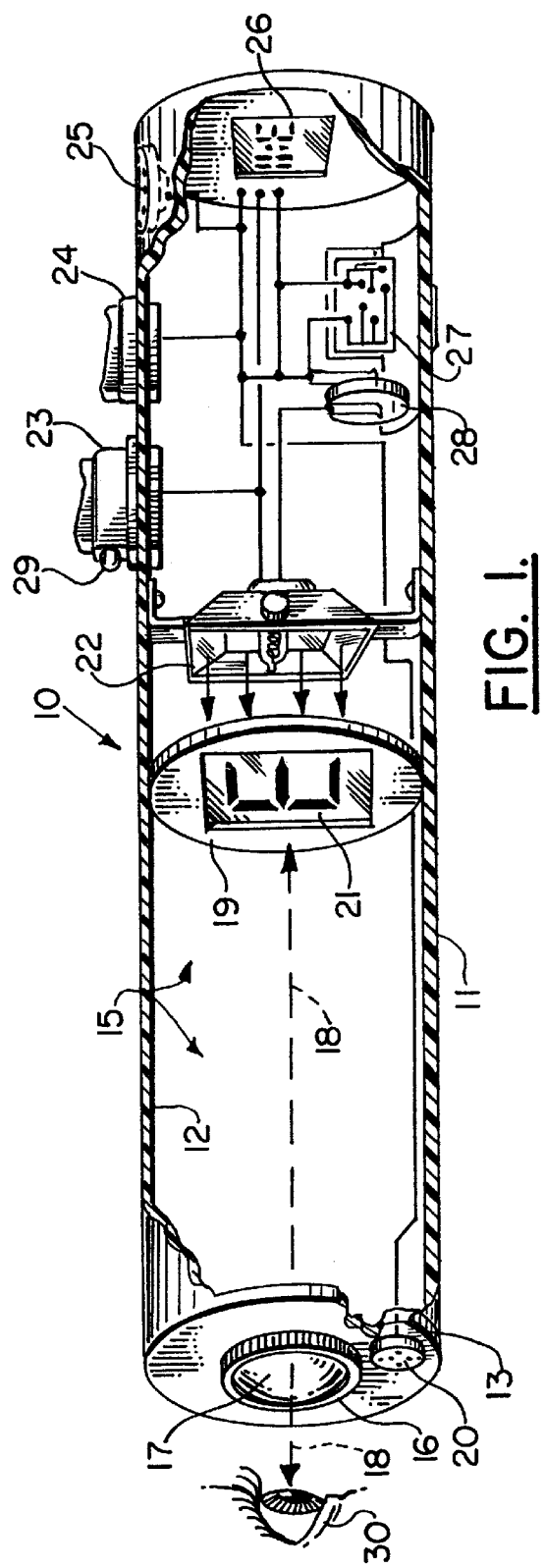
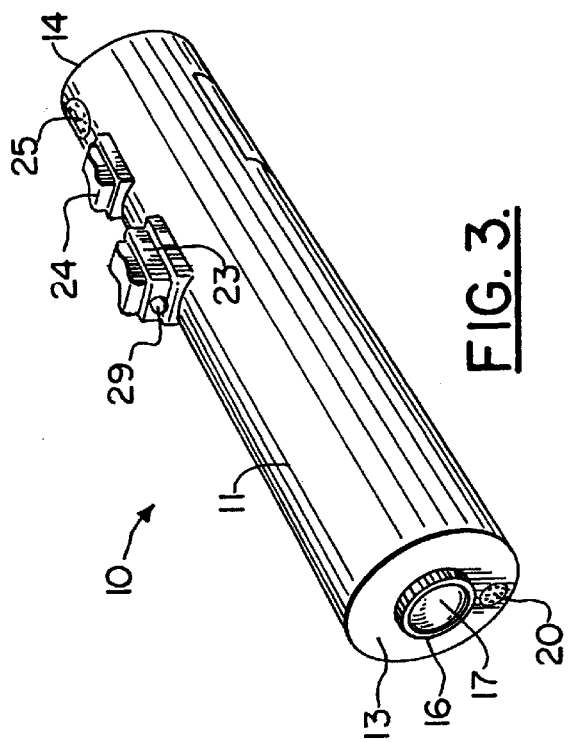
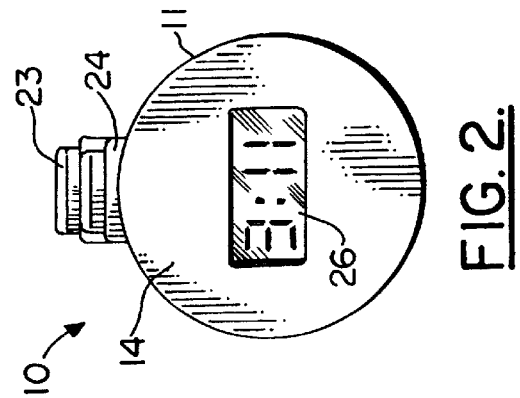

FLASH RECOVERY TIMER AND WARNING DEVICE

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to light flash recovery. More particularly, the present invention relates to a method and apparatus for using a flash recovery timer and warning device to monitor flash recovery.

2. General Background of the Invention

Ordinary work and household illumination levels provide little challenge to the vision tissue of the healthy eye to maintain continuous vision. Brighter light exposure such as looking at fluorescent tubes or bright flashes such as camera flashes can temporarily "flash-blind" or "snow-blind" the central retina. In healthy eyes, the central vision recovers within a few seconds from a single brief bright light exposure.

In the presence of eye diseases that produce either edematous swelling of the central retina or deterioration of some of the tissues in the central retina, the amount of time required to recover from such brief bright light exposure is prolonged, in some cases greatly prolonged. Examples of eye diseases that can produce prolonged flash recovery times include diabetes related retina disease (diabetic cystoid macular edema) and macular degeneration with macular edema and other changes. These diseases affect millions of Americans.

In the early stages of certain eye diseases, flash recovery times may not be prolonged. With changes or worsening of the disease such as the new appearance of tissue swelling or the appearance of a bad blood vessel with leakage or bleeding, the flash recovery time can be greatly prolonged. The early detection of disease appearing or worsening, which can be warned of by prolongation of flash recovery time, could assist patients in obtaining professional help earlier.

The following patents are incorporated herein by reference: U.S. Pat. Nos. 4,545,658; 5,080,478; 5,065,767; 4,764,007; 2,247,653; 3,684,355; 2,232,316; and 2,283,769.

U.S. Pat. No. 4,545,658 discloses a portable flash device designed to temporarily "blind" the eye, and record the time of recovery to normal.

U.S. Pat. No. 2,283,769 discloses eye testing by placing a bright light in the eyes and temporarily "blinding" the person, then measuring the recovery time.

U.S. Pat. Nos. 2,247,653, 5,080,478, 4,764,007 and 3,684,355 disclose devices for testing glare and darkness on the eyes and measuring recovery.

BRIEF SUMMARY OF THE INVENTION

The apparatus of the present invention solves the problems confronted in the art in a simple and straightforward manner. What is provided is an improved flash recovery timer and warning device.

The flash recovery timer of the present invention is equipped with an audible and visual warning signal to provide an instrument that is easy to understand and use. The present invention could assist persons at risk for deteriorating vision, detecting that deterioration early so that the patient can seek appropriate professional help. Early detection by an appropriate eye care professional could result in a much better chance of preserving vision.

The flash recovery timer and warning device of the present invention is preferably a hand-held electronic device using a bright flash to create a temporary glare-type vision blur to the eye to be tested. A target with a display (eg. letter) and timer determine the amount of time required for the eye to recover after the flash. The device has a voice chip that, in addition to the timer display, warns that the vision recovery time is unusually prolonged and professional help should be sought. Other clinical applications may be useful.

Prolongation of glare or flash recovery time has been recognized for over a century as a sign of trouble with the central retina. There are a number of central retinal problems that can occur in the course of chronic diseases such as macular degeneration and diabetes that can devastate central vision. In some but not necessarily all cases, early detection of these pathologic changes can assist eye care providers in preserving vision.

The Flash Recovery Timer and Warning Device of the present invention provides an easy to use and understand portable office and/or home testing method to give early warning about changes in the functional ability of the eye to recover from bright light exposure.

Many persons despite careful instruction in the doctor's office, do not follow through, either from lack of understanding or from lack of motivation or perceived need with checking the function of their eyes monocularly at home. This device offers a simple reminder of the importance of home testing. It also offers a simple way of actually performing the test.

The amount of light energy delivered to the ocular surface and macula is below the threshold of damage according to ANSI standards.

A base-line of recovery can be established for each eye either in the doctor's office or at the time of acquiring the instrument. It will then be very easy for the subject to determine that there has been a change (prolongation) of flash recovery time.

The timer will also have a pre-programmed upper limit recovery time. If that time is exceeded, a warning will sound.

The present invention thus provides a flash recovery timing apparatus of improved construction. The apparatus includes a tubular instrument body having a bore, first and second end portions and a generally cylindrically shaped or tubular wall.

An aperture is provided at the first end portion of the instrument body, a lens being mounted in the aperture.

A display is positioned within the bore at the focal length of the lens so that a patient can focus on the display by looking through the lens.

A strobe or like lighting means is positioned within the bore for generating a bright flash of light within the bore for use during a flash recovery test. A wiring harness is provided that includes one or more switches. One of the switches can be used to activate the strobe. One of the switches can also be used to activate a timer for measuring the patient's response time of viewing the display after the strobe is activated.

A stop is provided for stopping the timer responsive to the patient's ability to see the display, thus evidencing flash recovery.

The stop can include a voice activated timer that times the delay between the strobe flash and the patient's voice activation.

The display is preferably a variable target such as an LCD display that can display different visual images such as different letters or different numbers in sequence. The apparatus can provide a microphone on the instrument body next to the lens for use with the voice activation software carried in the computer.

A power source such as a battery can be a part of the instrument body so that the apparatus is self-contained and can be disposable after the battery has been drained with power.

The apparatus can include a computer that controls operation of the strobe, the display and the timer. The computer can also be used to provide voice recognition software that listens to the patient's voice through the microphone and talks after a test through a voice chip.

The present invention provides an improved method of measuring a patient's flash recovery time. The method steps include the providing of an instrument that includes an instrument body with a bore, a viewing aperture at one end of the bore, a strobe in the bore, a timer, a visual display within the bore, a computer and a wiring harness that includes one or more switches.

As part of the method, the patient views the display through the aperture. Using one of the switches, the strobe is fired t generate a light flash inside the bore.

A firing of the strobe simultaneously activates the timer. The patient indicates when the display can be seen after the light flash of step "c" thus providing an indication of flash recovery. The timer measures the elapsed time between the flash activation and the patient's ability to once again view the display.

A computer can be used to provide an audible indication of test failure if the measured elapsed time in seconds for example, exceeds a pre determined acceptable time value.

The visual display preferably changes between the time that the flash is generated and the patient recovers from the flash.

The method contemplates the instrument being provided with a voice chip and the voice chip speaks an audible message that the test has failed.

The method contemplates a microphone that is carried by the instrument body or which interfaces with the instrument body and its computer for listening to the patient's voice when the test is completed, as when the patient's flash recovery is complete and the patient is able to view the image. In such a situation, the patient reads the letter and the voice recognition software stops the timer if the patient correctly identifies the displayed letter or number.

The switches that are used as part of the instrument with the method can include an on/off switch and a reset switch. The instrument can include a microphone wherein the computer is voice activated by the microphone and the patient's voice. Alternatively, the patient can depress a switch to indicate that the display can be seen, thus stopping the timer to indicate that flash recovery is complete. The computer can compare the visual display with the patient's utterance and determines if the patient has correctly read the display. Thus, the display preferably changes from the time that the test begins until the patient is able to view the LCD display again. For example, a new letter can be displayed a few milliseconds after the strobe has flashed.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a cut-away, perspective view of the preferred embodiment of the apparatus of the present invention;

FIG. 2 is an end view of the preferred embodiment of the apparatus of the present invention; and FIG. 3 is a perspective view of the preferred embodiment of the apparatus of the present invention.

DETAILED DESCRIPTION OF THE INVENTION

The flash recovery timer and warning device 10 of the present invention is comprised of a tubular body 11 with a wall 12 that surrounds a hollow bore 15. Body 10 has first end portion 13 and second end portion 14. First end portion 13 provides a viewing aperture 16 with focusing lens 17. Focusing lens 17 fills the viewing aperture 16, allowing the patient 30 to see a selected display 21 (eg. letter E) on target 19 at the focal distance 18 of the lens 17. The target display letter can be variable. For example, the target 19 preferably consists of a clear LCD or similar material that allows a controlled variation in the stimulus display 21 (eg. letter) to be read.

Behind the target 19 sits a strobe 22 or like bright flash device activated by the push of a switch or button 23 positioned on wall 12 at the upper portion of body 11. When switch button 23 is depressed, the flash occurs and a timer 26 is started simultaneously. The patient 30 views the target 19 display 21 which should be immediately blurred out by the bright flash from strobe 22. The moment that the display (e.g. letter) 21 becomes clearly discernable through the glare, the patient 30 reads aloud the letter displayed which has been changed from the original focusing display letter 21 at the time of flash delivery by computer 27.

Computer 27 will use the audible saying of the letter viewed to determine both the time delay between strobe flash and the audible uttered by the patient 30. Microphone 20 picks up this audio and sends it to the computer 27 that is equipped with voice recognition software to verify that the subject has correctly identified the stimulus target. If the stimulus target has been incorrectly identified, the patient is prompted by voice chip 25 to repeat the test. If the timer 26 has gone past a predetermined, pre-set time limit, an audio warning will be activated at voice chip 25 instructing the patient, for example to "see the doctor".

The apparatus 10 can be reset by a push of the stop button 24.

The on/off and start switch button 23 contains an indicator light 29 as well as a connection with a voice chip 25 to indicate when the strobe 22 has charged sufficiently to discharge.

The apparatus 10 is preferably hand held and can be battery 28 powered. The apparatus 10 can be manufactured as a self-contained, disposable unit. The present invention also provides an improved method for testing a patient's flash recovery.

This improved method is initiated after the subject is informed of what sensations to expect and instructed in the operation of the device 10, the on/off switch 23 is placed into the "on" position. After a few seconds, the battery 28 will have charged the strobe 22. A small indicator 29 on the forward face of the on/off switch 23 will illuminate and the voice chip will sound "ready".

The patient 30 peers through the viewing aperture 16 and lens 17 to obtain a clear view of the target display letter 21. While watching the target letter, the switch 23 is depressed. This activates the strobe 22 causing temporary glare blindness. At this moment, target letter 21 is also changed by the computer 27. The timer display 26 at the rear of the device 10 (which was activated at flash delivery by the computer 27) records the elapsed time. The charging 26 indicator light 29 is cut off by the activation of the start button.

The patient 30 watches steadily through the viewing aperture 16, the center of the body 11. As soon as the target display letter 21 becomes discernable, the patient 30 reads the letter aloud, for example, "F". Simultaneously, the "stop" button is pushed by the patient. Alternatively, voice recognition software can be used to stop the timer if the correct letter is uttered by the patient. When the timer is stopped, it indicates the seconds of recovery from the strobe flash. If the recovery time is longer than a pre-determined interval, the voice chip 25 will be activated and the indicator light 29 will flash instructing the patient 30 to consult the eye doctor.

The apparatus 10 can be re-set so that it will be ready for use on the other eye. The same sequence is then repeated. After the apparatus 10 is used, it should be re-set with the stop/reset button 24 and powered off by moving the on/off start button into the "off" position.

Long-life batteries 28 can be used to power the apparatus 10. Each device can be disposable. Sufficient power will be provided for serial uses for approximately ½ year.

PARTS LIST

| PART NO | DESCRIPTION |
| --- | --- |
| 10 | fast recovery timer apparatus |
| 11 | tubular body |
| 12 | cylindrical wall |
| 13 | first end |
| 14 | second end |
| 15 | hollow bore |
| 16 | viewing aperture |
| 17 | lens |
| 18 | focal distance |
| 19 | target |
| 20 | microphone |
| 21 | display |
| 22 | strobe |
| 23 | switch (on-off) |
| 24 | switch (stop-reset) |
| 25 | voice chip |
| 26 | timer display |
| 27 | computer chip |
| 28 | battery |
| 29 | light |
| 30 | patient |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A flash recovery timing apparatus comprising:
   a) a tubular instrument body having a bore, first and second end portions, and a wall;
   b) an aperture at the first body end portion;
   c) a lens mounted in the aperture;
   d) a display positioned within the bore at the focal length of the lens so that a patient can focus on the display by looking through the lens;
   e) a strobe positioned within the bore for generating a bright flash of light within the bore;
   f) a switch for activating the strobe;
   g) a timer for measuring a patient's response time of viewing the display after the strobe is activated;
   h) stop means for stopping the timer responsive to the patient's ability to see the display, evidencing flash recovery;
   i) stop including a voice activated timer that times the delay between the strobe flash and the patient's voice activation.

2. The flash recovery timing apparatus of claim 1 wherein the display is a variable target that can display different images in sequence.

3. The flash recovery timing apparatus of claim 1 further comprising a microphone on the body that is positioned next to the patient during use.

4. The flash recovery timing apparatus of claim 1 further comprising a power source for powering the strobe.

5. The flash recovery timing apparatus of claim 1 further comprising a computer that controls operation of the strobe, the display and the timer.

6. The flash recovery timing apparatus of claim 1 wherein the switch is a manually operable switch.

7. The flash recovery timing apparatus of claim 1 further comprising a reset switch for zeroing the timer.

8. The flash recovery timing apparatus of claim 1 further comprising a timer display for displaying a time value.

9. The flash recovery timing apparatus of claim 1 wherein the display includes a liquid crystal diode.

10. A flash recovery timing apparatus that can display a number of different letter or number symbols;
    a) an instrument body having an interior cavity;
    b) the body having an aperture with a lens;
    c) the cavity having a display that displays an image;
    d) a timer;
    e) a light source positioned within the cavity for generating a flash of bright light within the cavity;
    f) a switch that activates the timer and the light source to illuminate the light source for a short time;
    g) a microphone on the body;
    h) a voice activated computer for stopping the timer to display an elapsed time value responsive to sounds uttered by the user.

11. A flash recovery timing apparatus that can display a number of different letter or number symbols;
    a) an instrument body having an interior cavity;
    b) the body having an aperture with a lens;
    c) the cavity having a display that displays an image;
    d) a timer;
    e) a light source positioned within the cavity for generating a flash of bright light within the cavity;
    f) a switch that activates the timer and the light source to illuminate the light source for a short time;

g) a microphone on the body;

h) a patient activated computer that stops the timer when the patient recovers from the flash sufficiently to view the image.

12. A method of measuring a patient's flash recovery time, comprising the steps of:

a) providing an instrument that includes an instrument body with a bore, a viewing aperture at one end of the instrument body, a strobe in the bore, a timer, a visual display, a computer, and a wiring harness that includes one or more switches;

b) having the patient view the display through the aperture;

c) firing the strobe to generate a light flash inside the bore;

d) simultaneously activating the timer when the flash is activated in step "c";

e) having the patient indicate when the display can be seen after the light flash of step "c";

f) measuring the elapsed time between steps "c" and "e"; and g) using the computer to provide an audible indication of test failure if the measured elapsed time in step "f" exceeds a predetermined acceptable time value.

13. The method of measuring a patient's flash recovery time of claim 12 wherein the visual display changes between steps "b" and "e".

14. The method of measuring a patient's flash recovery time of claim 12 wherein the instrument includes a voice chip and in step "g" the voice chip speaks an audible message if the test is failed.

15. The method of measuring a patient's flash recovery time of claim of claim 12 wherein the instrument includes a microphone and in steps "e" and "f" the computer is voice activated by the microphone and the patient's voice.

16. The method of measuring a patient's flash recovery time of claim 12 wherein the switches include and on-off switch, and in step "c" the patient presses the on-off switch.

17. The method of measuring a patient's flash recovery time of claim 16 wherein instrument includes a microphone and in steps "e" and "f" the computer is voice activated by the microphone and the patient's voice.

18. The method of measuring a patient's flash recovery time of claim 12 wherein in step "e" the patient depresses a switch to indicate that the display can be seen.

19. The method of measuring a patient's flash recovery time of claim 12 wherein in step "c" the patient reads the visual display and the computer to stop the timer.

20. The method of measuring a patient's flash recovery time of claim 19 wherein in step "c" the computer compares the visual display with the patient's utterance and determines if the patient has correctly read the display.

21. The method of measuring a patient's flash recovery time of claim 20 wherein the timer measures the elapsed time if the computer determines that the patient has correctly read the display.

* * * * *